US00H002268H

(19) United States
(12) Statutory Invention Registration
Gutting et al.

(10) Reg. No.: US H2268 H
(43) Published: Apr. 3, 2012

(54) MICROTITER PLATE TO MITIGATE CELL DISTRIBUTION BIAS FROM MENISCUS EDGE

(75) Inventors: Bradford W. Gutting, Spotsylvania, VA (US); Ryan S. Mackie, Spotsylvania, VA (US); George A. Andrews, Jr., Fredericksburg, VA (US)

(73) Assignee: The United States of America, as represented by the Secretary of the Navy, Washington, DC (US)

(21) Appl. No.: 12/322,958

(22) Filed: Jan. 30, 2009

(51) Int. Cl.
*C12M 1/00* (2006.01)

(52) U.S. Cl. ..... 435/305.3

(58) Field of Classification Search ..... 435/305.3, 435/288.4

See application file for complete search history.

(56) References Cited

U.S. PATENT DOCUMENTS

| | | | | | |
|---|---|---|---|---|---|
| 4,599,314 | A | * | 7/1986 | Shami | 435/305.3 |
| 4,599,315 | A | | 7/1986 | Terasaki et al. | 435/301 |
| 4,829,006 | A | | 5/1989 | Smith et al. | 435/301 |
| 5,002,889 | A | | 3/1991 | Klein | 356/39 |
| 5,741,463 | A | * | 4/1998 | Sanadi | 422/527 |
| 6,074,614 | A | | 6/2000 | Hafeman et al. | 422/102 |
| 6,581,761 | B1 | | 6/2003 | Stafford et al. | 206/5.1 |
| 6,716,350 | B2 | | 4/2004 | Olivier et al. | 210/326.1 |
| 7,169,577 | B2 | * | 1/2007 | Wang et al. | 435/288.4 |
| D562,463 | S | | 2/2008 | Berndt et al. | D24/226 |
| 2001/0007642 | A1 | | 7/2001 | Feiglin | 422/102 |
| 2003/0032002 | A1 | * | 2/2003 | Wang et al. | 435/4 |
| 2003/0124029 | A1 | * | 7/2003 | Webb et al. | 422/102 |
| 2003/0235519 | A1 | | 12/2003 | Sha et al. | 422/102 |
| 2004/0009583 | A1 | | 1/2004 | Benn et al. | 435/287.2 |
| 2006/0029524 | A1 | | 2/2006 | Carter et al. | 422/101 |
| 2010/0197004 | A1 | * | 8/2010 | Gutting et al. | 435/305.3 |

* cited by examiner

*Primary Examiner*—Daniel Pihulic
(74) *Attorney, Agent, or Firm*—Gerhard W. Thielman

(57) ABSTRACT

A lid assembly is provided for mitigation or removal of meniscus along the periphery of sample liquid in the cavity wells of a microtiter plate. The assembly includes a lid plate having a mount surface, an array of plugs corresponding to the array of wells, and a plurality of posts. Each plug extends below from the mount surface and is insertable into the periphery of a counterpart well for contact with the liquid. The plurality of posts suspends the lid plate above the microtiter plate. Each post optionally passes through an orifice through the mount surface, with each post including an adjustable clamp to support the lid plate. The mount surface optionally includes an array of cavities that correspond in disposition to the array of plugs. Each plug is independently insertable through the mount surface to adjust depth of each plug into its counterpart well.

3 Claims, 9 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

MICROTITER PLATE TO MITIGATE CELL DISTRIBUTION BIAS FROM MENISCUS EDGE

STATEMENT OF GOVERNMENT INTEREST

The invention described was made in the performance of official duties by one or more employees of the Department of the Navy, and thus, the invention herein may be manufactured, used or licensed by or for the Government of the United States of America for governmental purposes without the payment of any royalties thereon or therefor.

BACKGROUND

The invention relates generally to meniscus removal or mitigation in cavity wells of a microtiter plate for improved homogeneity of biological cell distribution. In particular, the invention provides devices to suppress or redistribute surface tension effects of the liquid contained in the wells.

Multiwell or microtiter plates, are ubiquitous in biological and pharmaceutical research. A microtiter plate (also known as "microplate") represents a flat plate with multiple uniform "wells" used as small test tubes. The microplate has become a standard tool in analytical research and clinical diagnostic testing laboratories.

SUMMARY

Conventional wells in a microtiter plate yield disadvantages addressed by various exemplary embodiments of the present invention. In particular, various exemplary embodiments provide a lid assembly for superposition above the microtiter plate to mitigate or remove the meniscus along the periphery of sample liquid in the cavity wells of a microtiter plate. The assembly includes a lid plate having a mount surface, an array of plugs corresponding to the array of wells, and a plurality of posts.

In various exemplary embodiments, each plug extends below from the mount surface and is insertable into the periphery of a counterpart well for contact with the liquid. The plurality of posts suspends the lid plate above the microtiter plate. In various exemplary embodiments, each post optionally passes through an orifice through the mount surface, with each post including an adjustable clamp to support the lid plate. In alternate exemplary embodiments, the mount surface optionally includes an array of cavities that correspond in disposition to the array of plugs. Each plug is independently insertable through the mount surface to adjust depth of each plug into its counterpart well.

BRIEF DESCRIPTION OF THE DRAWINGS

These and various other features and aspects of various exemplary embodiments will be readily understood with reference to the following detailed description taken in conjunction with the accompanying drawings, in which like or similar numbers are used throughout, and in which.

DETAILED DESCRIPTION

In the following detailed description of exemplary embodiments of the invention, reference is made to the accompanying drawings that form a part hereof, and in which is shown by way of illustration specific exemplary embodiments in which the invention may be practiced. These embodiments are described in sufficient detail to enable those skilled in the art to practice the invention. Other embodiments may be utilized, and logical, mechanical, and other changes may be made without departing from the spirit or scope of the present invention. The following detailed description is, therefore, not to be taken in a limiting sense, and the scope of the present invention is defined only by the appended claims.

Figure 1:
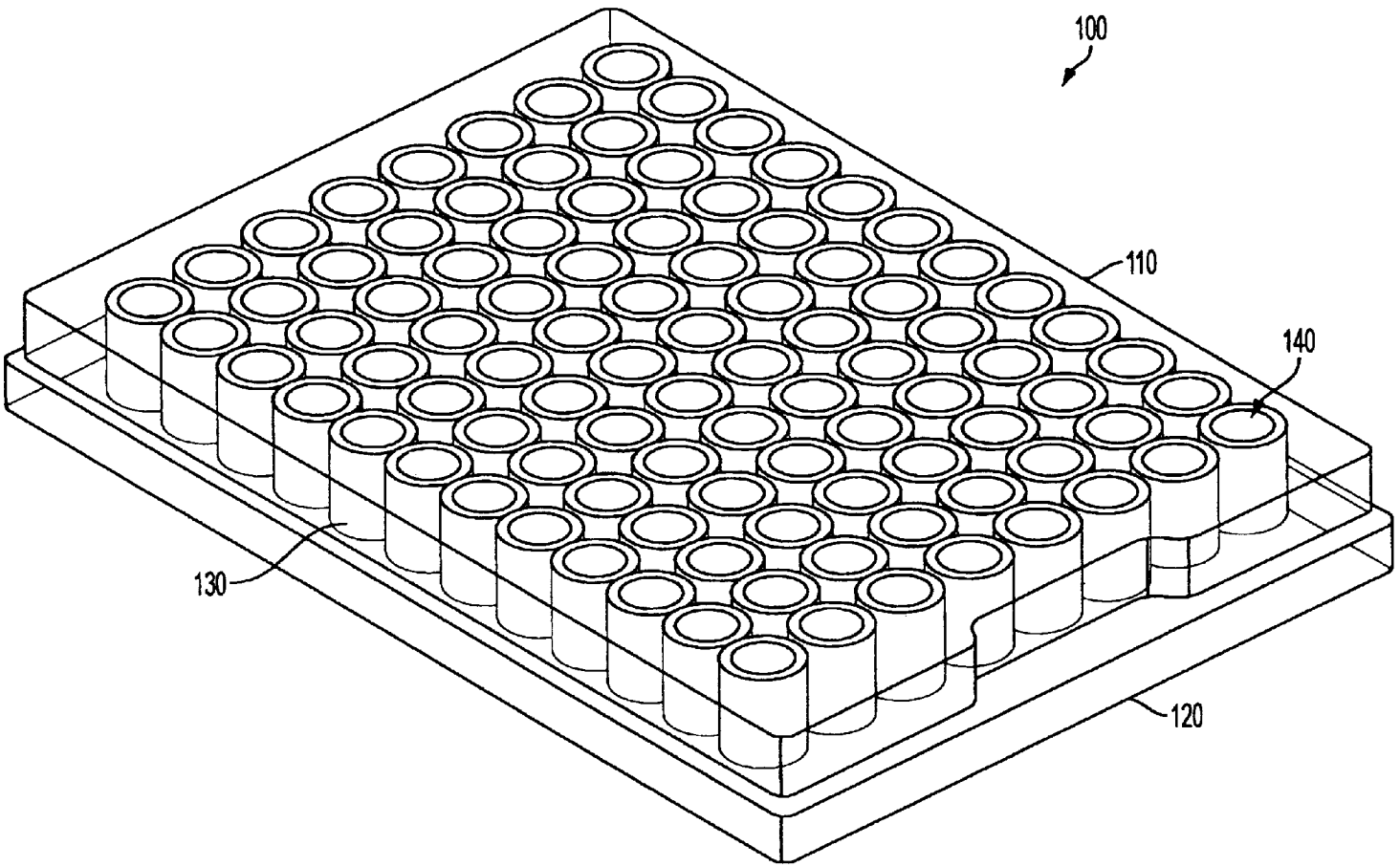
FIG. 1 RELATED ART
FIG. 1 is an isometric view of a multiwell microtiter plate.

FIG. 1 presents an isometric view 100 of a generic 96-well micro- titer plate 110 supported on a base 120. The microplate 110 features an array with eight columns and twelve rows of cavity wells 130. Each well 130 of this plate array holds a working volume of 300 μL fillable through the opening 140 with a liquid solution containing biological particulates, such as mammalian cells, bacteria, viruses, proteins, etc. These suspensions are initially prepared to be homogeneous via mixing before injection into the well 130 of the plate 110.

Such devises allow researchers to perform optical and spectroscopic analysis on biological samples by submersing them within various fluidic environments. Accordingly, maximal control of the sedimentation process is desirable so as to provide as much uniformity as possible both within individual wells and throughout the entire plate.

Figure 2:
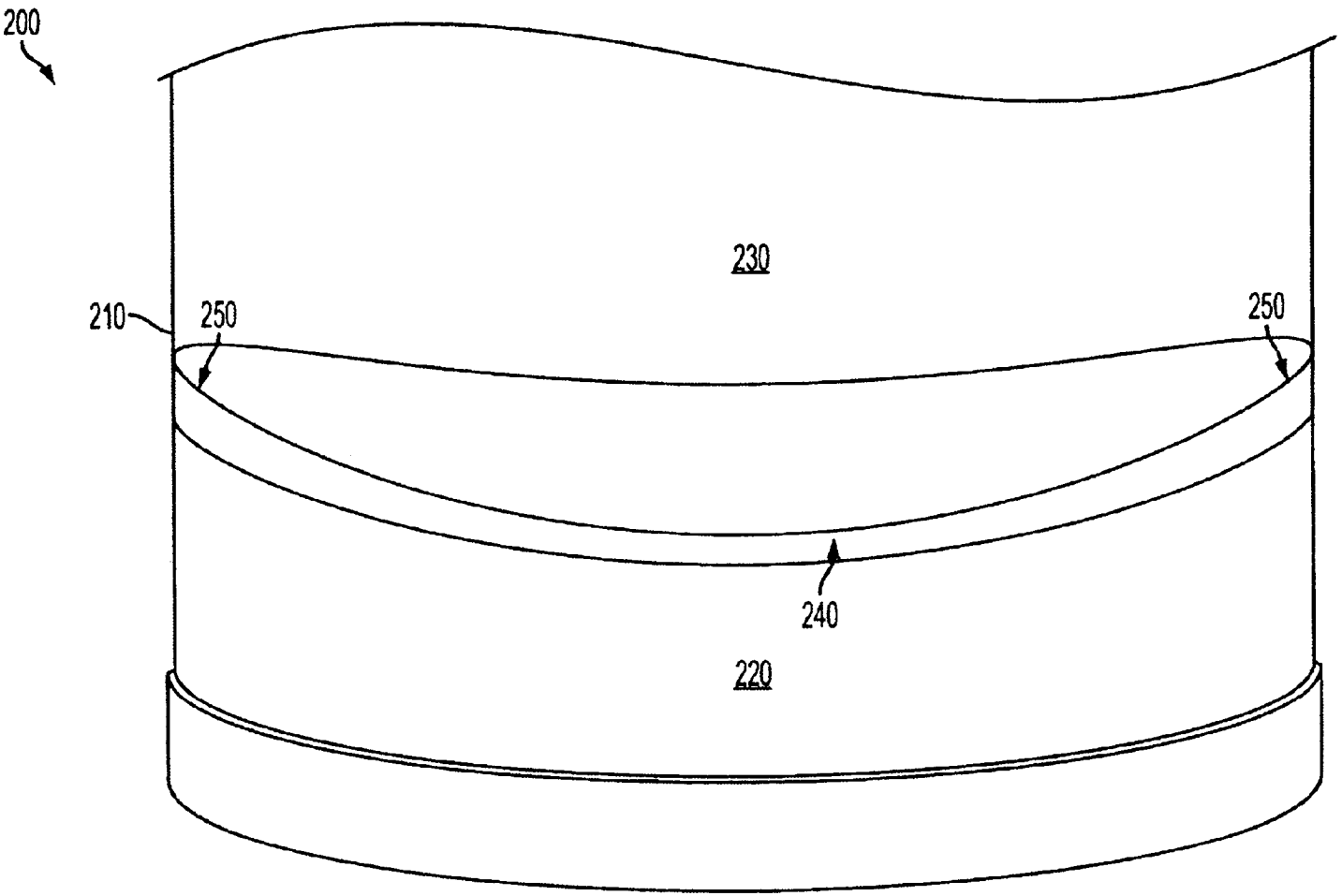
FIG. 2 is a detail elevation view of a well in a microtiter plate.

FIG. 2 shows an elevation view photograph 200 of a circular well 210 partially filled by liquid 220 with the remaining volume above containing air 230. The liquid represents the solution containing sample particulates for analysis. An interface surface 240 separates the boundaries of the liquid 220 and air 230. Additionally, the liquid 220 contacts the solid-wall boundary at the lateral and bottom peripheries of the well 210.

Due to surface tension of the liquid 220, the interface 240 exhibits curvature between the lateral periphery and the center of the well 210 for typical sample sizes. The curvature can be concave or convex depending on the contact angle between the liquid and the peripheral boundary. This phenomenon is most pronounced by the meniscus rise 250 along the edges adjacent the boundary of the well 210, thereby producing a concave curvature.

Figure 3:
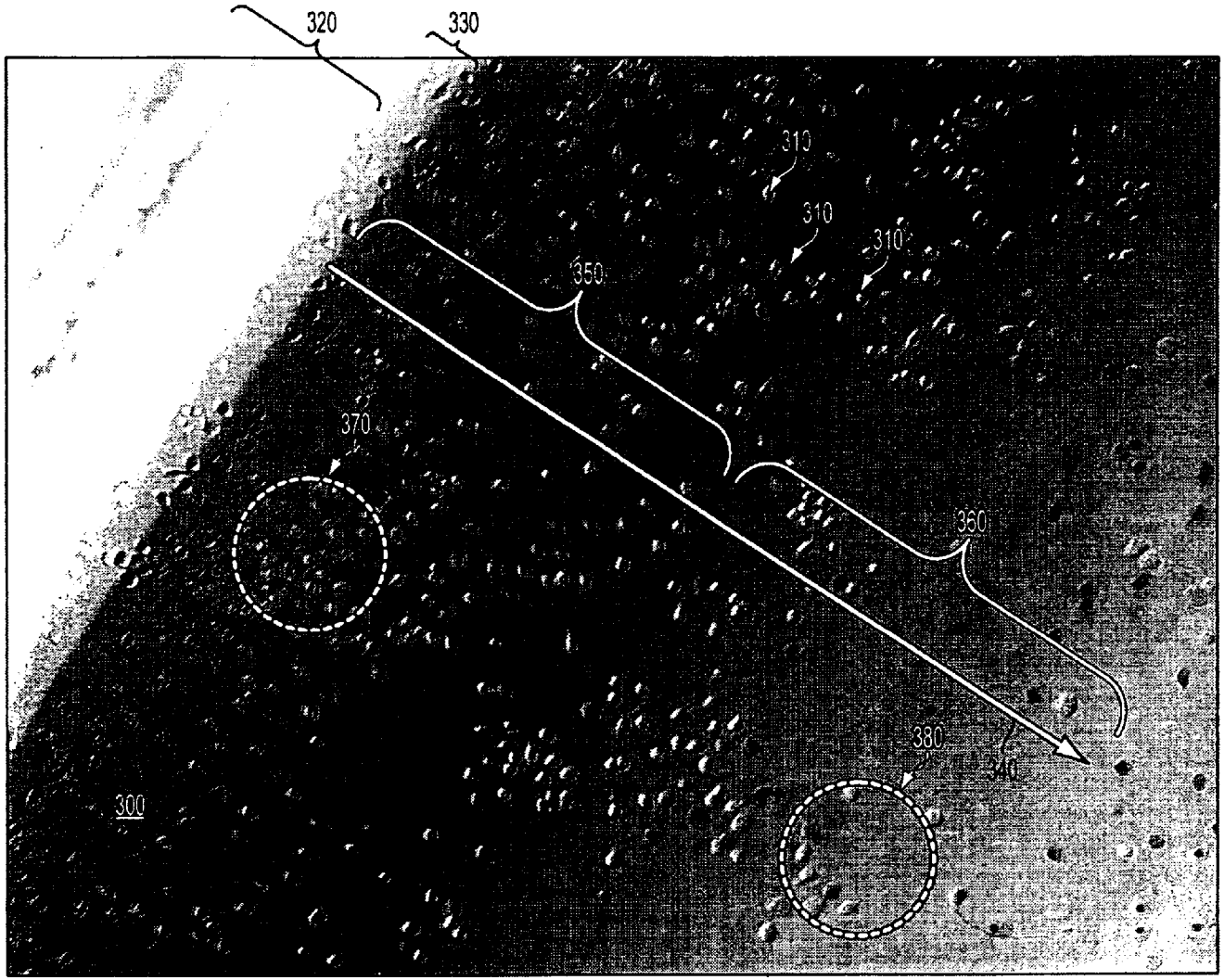
FIG. 3 is a detail plan view of a well with macrophage cells.

FIG. 3 shows a plan view detail photograph 300 of liquid contents of the well 210 containing the solution with J77A.4 macrophage cells 310 suspended therein. A circular periphery 320 bounds the well with an edge 330 at which meniscus forms. A directional vector 340 denotes the cell gradient from the well's peripheral edge 330 with higher cell density region 350 toward its center with lower cell density region 360. A proximal circular sample area 370 exhibits at least forty cells 310, whereas by contrast a distal circular sample 380 reveals fewer than ten cells 310.

Non-uniform sedimentation of cells 310 yields a survival consequence such that those that settle within the meniscus edge 330 region (with many neighbors) survive (as indicated by lighter shade), whereas those in the other regions 350 and 360 toward the center (with few neighbors) perish (as denoted by darker shade).

Figure 4C:
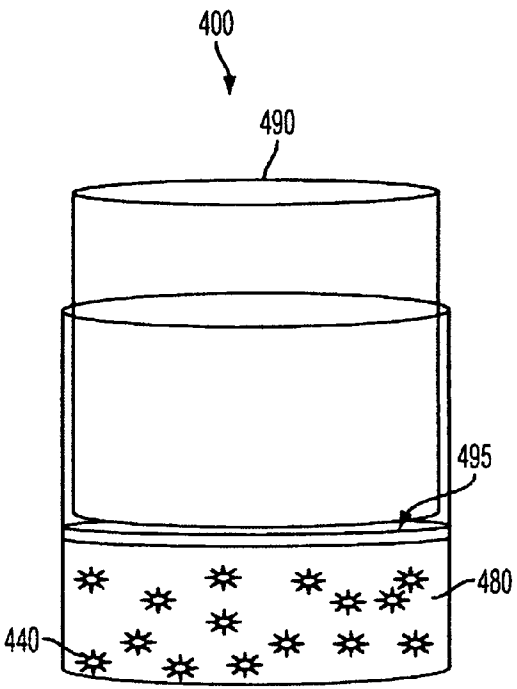
FIGS. 4B and 4C are isometric views of wells with meniscus mitigation.
Figure 4B:
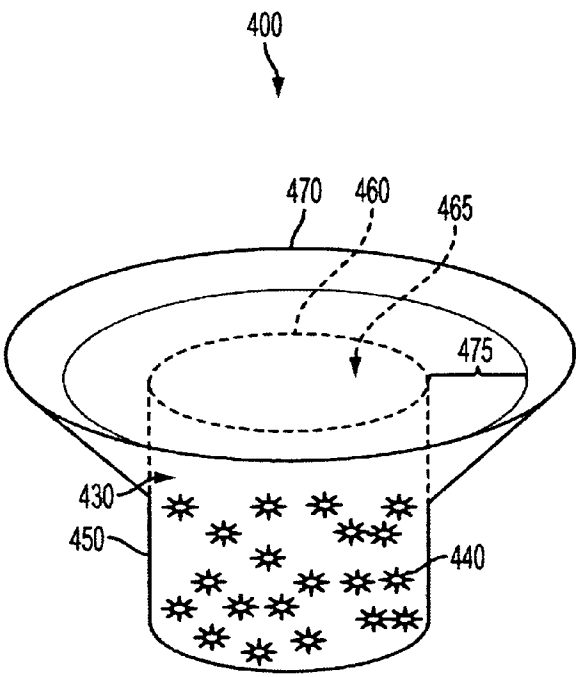
Figure 4A:
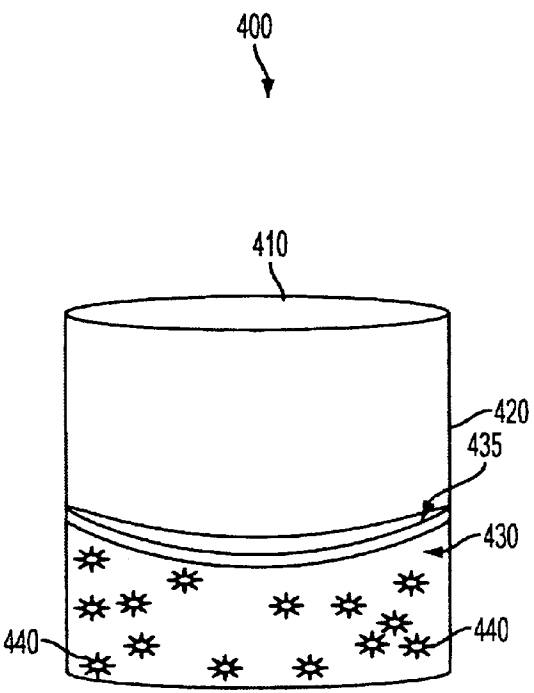
FIG. 4A is an elevation view of a well lacking meniscus mitigation.

FIGS. 4A, 4B and 4C present isometric diagrams 400 of well configurations. FIG. 4A shows an unmodified well 410 with a circular periphery 420 to contain a liquid 430 bounded by a surface meniscus 435. Within the liquid 430 are macrophage cells 440, which in the well 410 remain clustered near the periphery 420.

FIG. 4B shows an exemplary embodiment of a modified well 450 with a cylindrical section 460 that segregates a center core chamber 465 and a conical bevel 470 that segregates a peripheral annular chamber 475. Both chambers 465 and 475 can contain the liquid 430. In the modified well 450, the meniscus 435 distributes over a larger area in the annular chamber 475, thereby reducing its average curvature, especially toward the well's core chamber 465.

This technique can be labeled as a beveled-well meniscus-reduction microplate to reduce the degree of meniscus curvature by confining the outer periphery that adjoins a boundary to an annular bevel portion. The liquid surface spans across a wider extent within the bevel 470, thereby flattening the surface 435 within the section 460. The reduced curvature of the liquid surface homogenizes cell distribution within the well 450.

FIG. 4C shows another exemplary embodiment of a modified well 480 featuring a lid plug 490 that negates the meniscus by providing a solid fixed surface 495 onto which surface tension forms a flat profile. Both of these exemplary wells 450 and 480 yield more uniform distribution of cells 440 as a consequence of meniscus mitigation.

This technique can be labeled as a meniscus-suppression lid applicable for either fixed or variable liquid volume. The lid employs a plug 490 that protrudes into the well 480. The plug's terminating surface 495 contacts the surface of the liquid 430 contained in the well 480, thereby removing the meniscus curvature. Special coatings can be employed on the surface 495 to inhibit material of the liquid 430 from adhering to the plug 490. Typical microtiter plates (having arrays of 6, 12, 24, 48, 96 and 384 wells) can remain unmodified for this embodiment. Instead, a researcher merely obtains lid inserts to use with commercially-available microplates.

Figure 5:
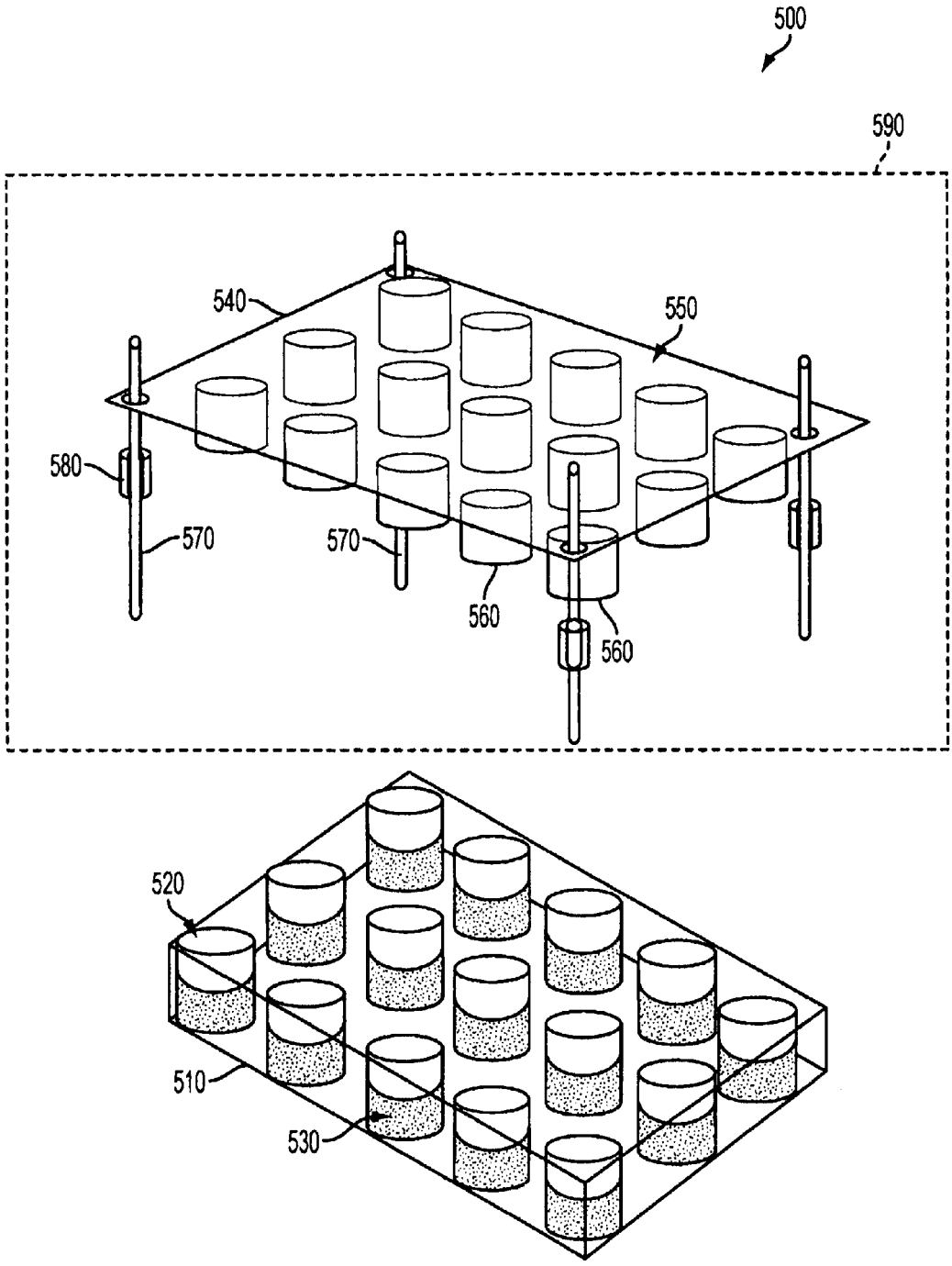
FIG. 5 is a first isometric view of a microtiter plate with a lid plate having fixed plugs.

FIG. 5 illustrates an isometric view 500 of an exemplary plate with accompanying lid. A microplate 510 includes an array of cavity wells 520 (open at their tops), each well containing a uniform volume of liquid 530. A lid plate 540 having a mount surface 550 is superpositioned above the microplate 510. An array of plugs 560 extend below the surface 550.

These plugs 560 correspond to and are disposed above the wells 520 to suppress meniscus formation in their liquid contents 530. A set of displacement posts 570 provide support adjacent the outer corners of the lid plate 540. Each post 570 includes a translatable clamp 580 to adjust the position of the lid plate 540 from the microplate 510 or its support platform.. The combination of lid plate 540, plugs 560, posts 570 and clamp 580 represent a lid assembly 590 to retrofit with a conventional plate 520.

Each plug 560 insertably fits into its corresponding well 520. For circular geometries, the plug's outer diameter is therefore less than the well's inner diameter. Preferably, the plug's outer diameter is only slightly smaller than the well's inner diameter to minimize meniscus effects.

Figure 6:
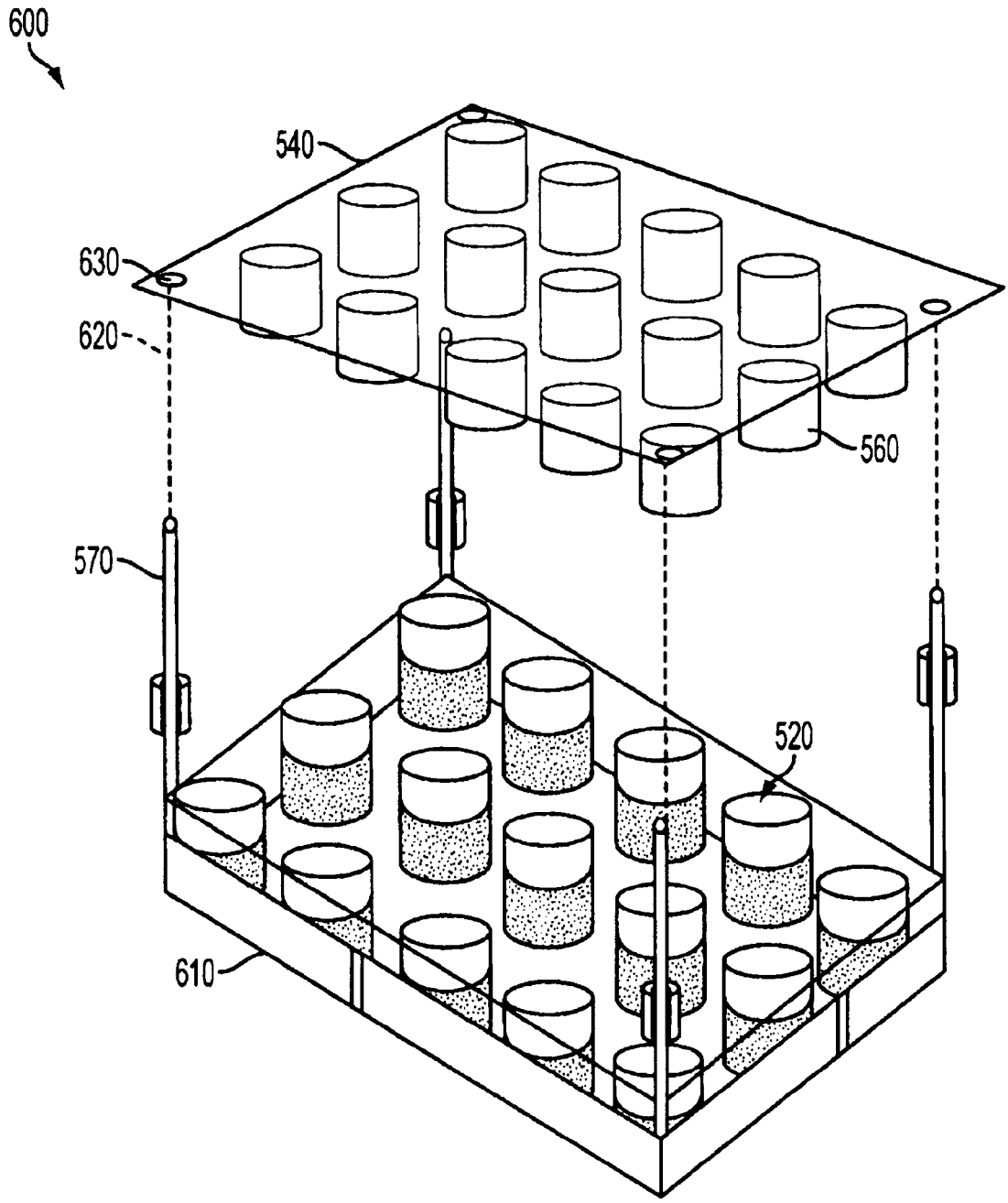
FIG. 6 is a second isometric view of the microtiter and lid plates.

FIG. 6 shows an isometric view 600 of the exemplary plate with the accompanying lid assembly 590 for equal volume content in the wells 520. A bracketing tray 610 (optionally adjustable) for the microplate 510 provides a platform for the posts 570. The lid plate 540 aligns to the posts 570 along coaxial lines 620. Each post 570 passes through a corresponding orifice 630 in the lid plate 540.

The clamps 580 support the lid plate 540 along their corresponding posts 570 to be disposed above the microplate 510. The clamps 580 can be adjusted to enable the plugs 560 to be disposed within their corresponding wells 520, thereby suppressing meniscus formation within their liquid contents 530.

Figure 7:
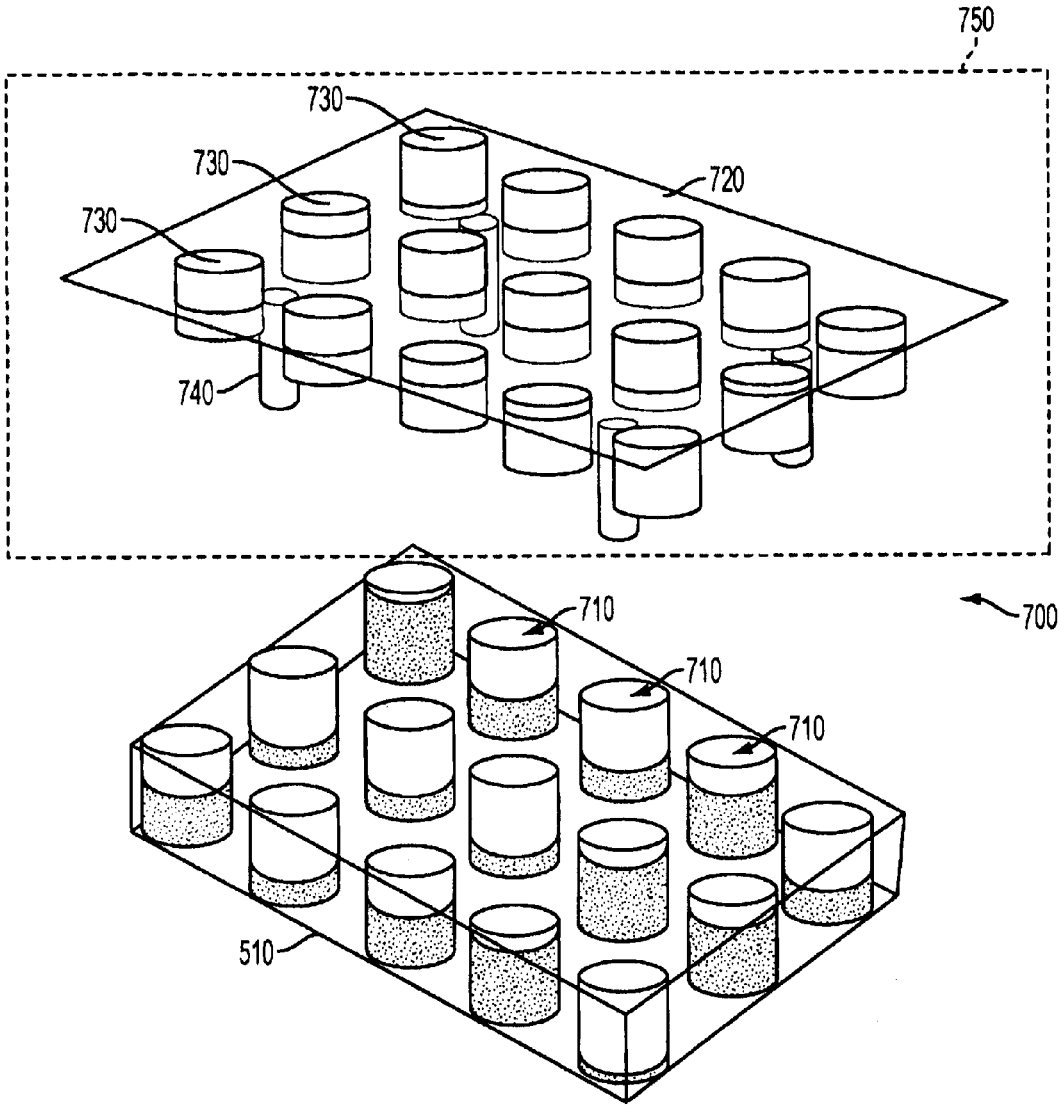
FIG. 7 is an isometric view of a microtiter plate with a lid plate having adjustable plugs.

FIG. 7 illustrates an isometric view 700 of an exemplary plate with an accompanying lid in an alternate embodiment. A microplate 510 includes an array of wells 520 (open at their tops), each well containing a volume of liquid 710 that varies from well to well. A lid plate 720 is suspended above the micro- plate 510. The lid plate 720 includes an array of plugs 730 that corresponds to the wells 520.

Each plug 730 can be vertically adjusted relative to the surface of the lid plate 720. A series of support columns 740 extend below the lid plate 720. The combination of lid plate 720, plugs 730 and columns 740 represent a lid assembly 750 to retrofit with a conventional plate 510. The columns 740 engage the microplate 510 in gaps between adjacent wells 520 to suspend the lid plate 710 above the microplate 510. The disposition of plug 730 extending from the lid plate 720 is tailored to descend into its corresponding well 520 to that specific depth so as to suppress the meniscus in that liquid content 710.

Figure 8A:
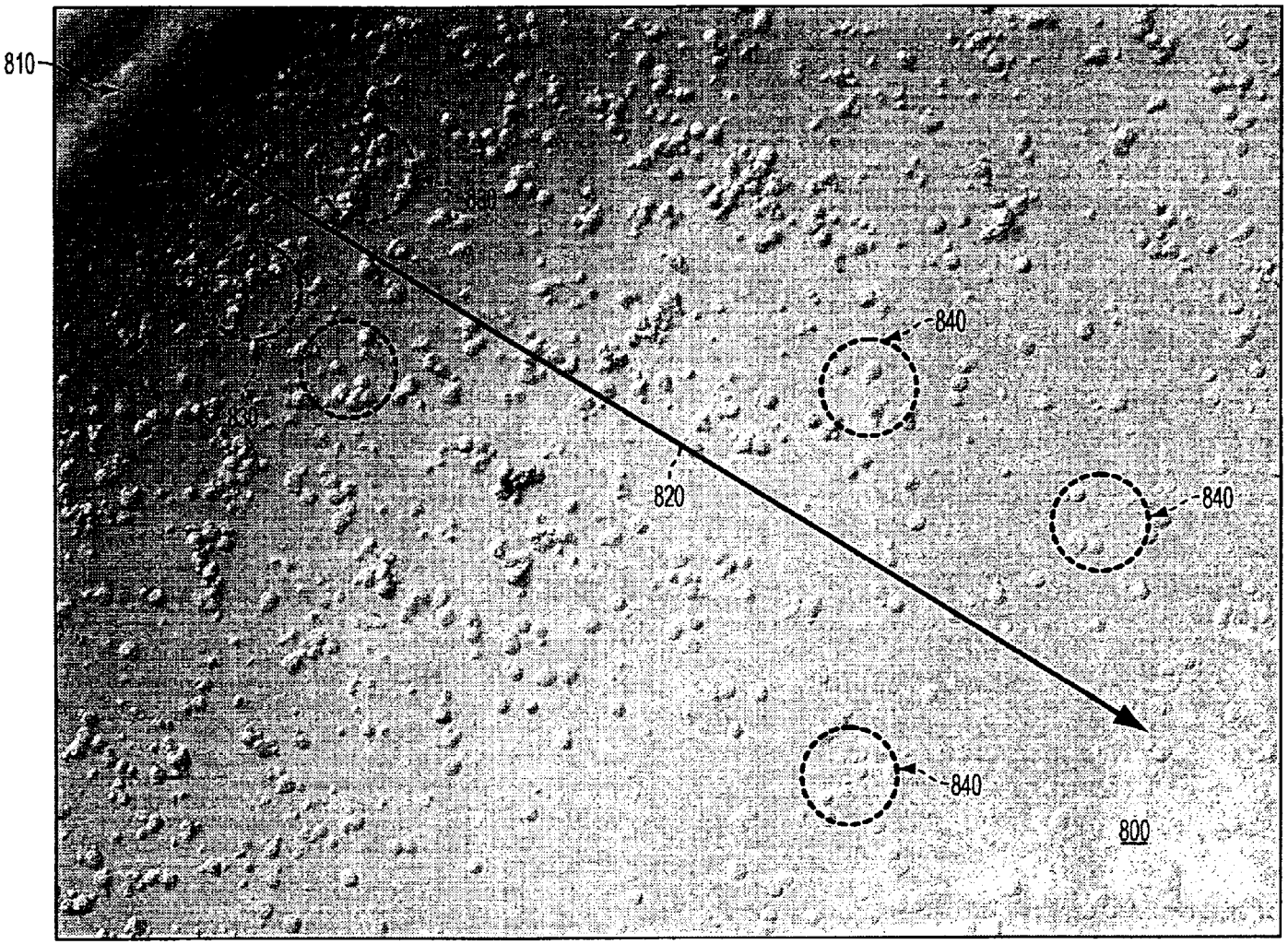
FIG. 8A is a detail plan view of a well showing cell distribution without meniscus mitigation.
Figure 8B:
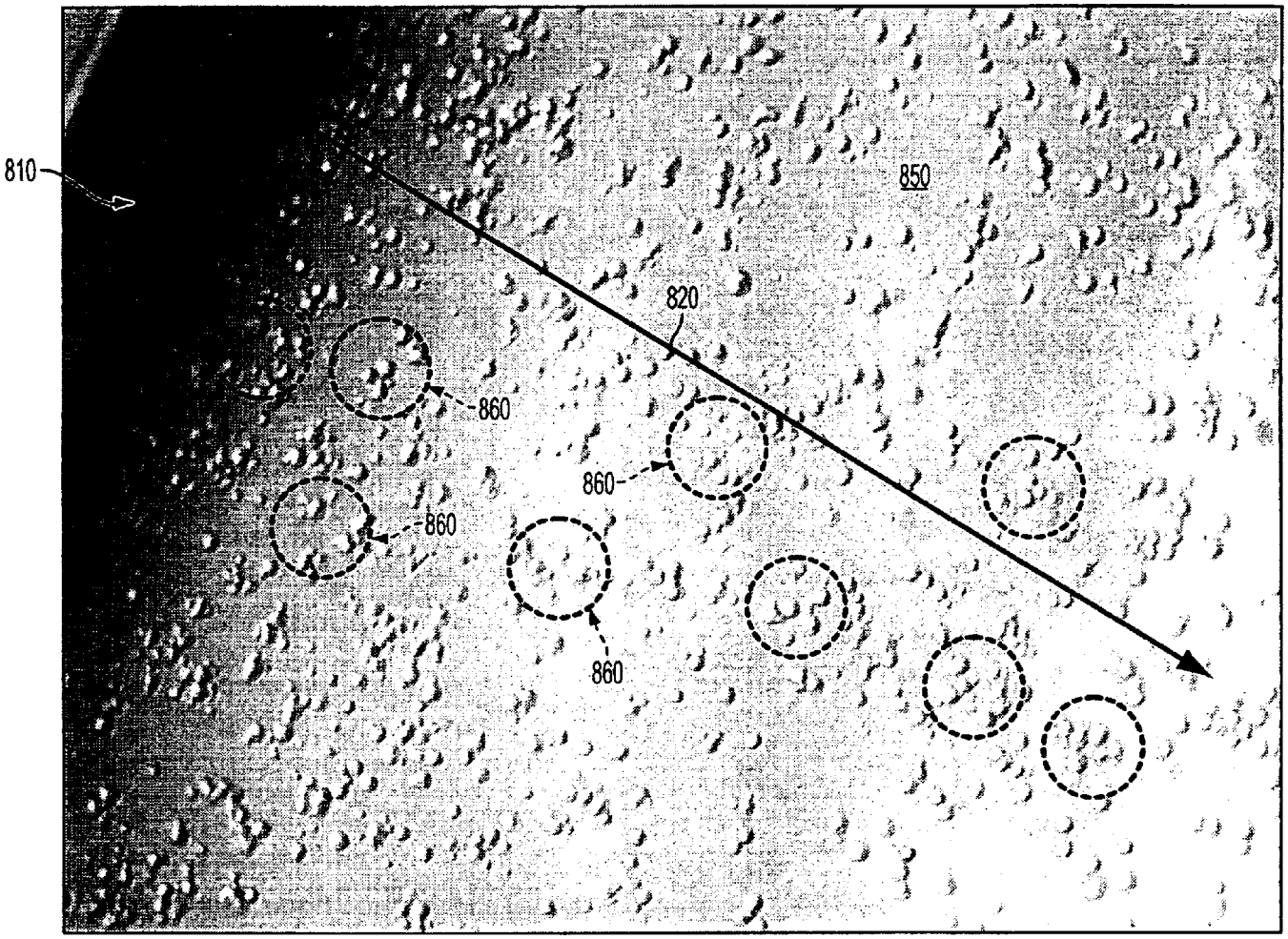
FIG. 8B is a detail plan view of a well showing cell distribution with meniscus mitigation.

FIGS. 8A and 8B show plan view detail photographs of liquid contents of a well containing liquid and macrophage cells suspended therein. In particular, FIG. 8A presents a photograph 800 identifying a circular wall 810 of the well and a vector 820 leading to its center. Conditions for FIG. 8A are substantially analogous to those displayed in FIG. 3 without meniscus mitigation.

Near the wall 810, proximate cells 830 cluster together in greater density than distal cells 840 towards the center. By contrast, FIG. 8B demonstrates cell distribution effect from meniscus mitigation in a photograph 850, also showing the wall 810. Distribution of cells 860 exhibits considerable uniformity along the vector 820.

By suppressing meniscus formation in well liquid, cell distribution uniformity can be augmented. This can be accomplished by engaging a lid plug 480 against the liquid at its top surface. Alternatively, this can also be accomplished by providing radially segregated chambers at the liquid surface. These chambers can be bounded by an upper cylinder 460 for the cells under evaluation and a bevel cone 470 for diverting the meniscus by its extension.

The efforts leading to the described embodiments are directed to providing tissue culture plates that mitigate differential stacking of cells towards the well's periphery. The photograph 300 illustrates effects of cell stacking. In addition to there being more cells on the perimeter 310 of the well 210, the cells 320 towards the middle are dead as indicated by the stain from the darkening (blue) dye.

These untreated cells 320 were seeded in the well 210, washed, and deposited in the incubator for an interval. This heterogeneous pattern also extends to treated cells. Various exemplary embodiments present techniques to distribute the cells 320 homogeneously on the bottom of the well 210 in the plate 110. The principle options include modifying the well to expand the meniscus and incorporating a lid to conform the meniscus to a flat solid surface.

For a multiwell microplate in which each well 520 contains equal volumes, the configuration of the lid assembly 590 shown in views 500 and 600 is appropriate. This application, in which overall plate volume changes are required for different experiments, employs the lid 540 for constant-volume meniscus removal with fixed plugs 560. Each plug 560 has the same dimension and extension from the lid surface 550 being permanently attached thereto.

Adjustability for different overall meniscus heights for different experiments can be achieved by sliding the entire lid 540 upon the posts 570 that protrude through orifices 630 in the lid 540 and include adjustably translatable clamps 580 capable of supporting the lid's weight at a desired height. To avoid splay, the posts 570 can optionally interface with the bracketing tray 610, which can be designed for adaptability to enclose standard microplates 510 of various sizes or else be rigid for a fixed configuration.

For a multiwell plate in which each well 710 contains a different volume, the configuration of the lid assembly 750 shown in view 700 can be implemented. In this application, the lid plate 720 has an array of cavities, and each plug 730 individually slides through its corresponding cavity, such as by pushing with a finger. The lid plate 720 has support columns 740 that remain fixed in position to provide a constant separation from the microplate 510 enabling for maximum penetration of any particular plug 730 to the bottom of any given well 710.

The dimensions of the extruding plugs 560 and 730 need not fill the entire corresponding well 520 and 710. Although such variation might affect the meniscus response, plugs narrower than the inner region of the well may exhibit advantages in production cost and reduced surface interaction. Additionally, a single plug may be replaced with multiple smaller plugs whose adjustability can be individually customized for either the lid plate 720 or within a sub-plug platform inserted in lieu of the plug 730.

While certain features of the embodiments of the invention have been illustrated as described herein, many modifications, substitutions, changes and equivalents will now occur to those skilled in the art. It is, therefore, to be understood that the appended claims are intended to cover all such modifications and changes as fall within the true spirit of the embodiments.

What is claimed is:

1. A microtiter plate for containing sample liquid, comprising;

a base platform;

a sample plate disposed on said platform; and an array of cavity wells disposed on said sample plate, each well having a periphery for containment of the liqud, wherein said periphery includes:

a cylindrical chamber extending upward from said platform to an intermediate height between said platform and a terminus height, and a conic bevel chamber extending upward and radially outward from said cylindrical chamber from said intermediate height to said terminus height, wherein said well can contain the liquid in both said cylindrical and bevel chambers.

2. The microtiter plate according to claim 1, wherein said each well has a flat bottom bounded by said platform.

3. The microtiter plate according to claim 1, further including a lid plate having an array of plugs, each plug corresponding to said each well.

* * * * *